US009427326B2

(12) United States Patent
Hewko

(10) Patent No.: US 9,427,326 B2
(45) Date of Patent: Aug. 30, 2016

(54) SPINAL IMPLANT

(71) Applicant: GLOBUS MEDICAL, INC., Audubon, PA (US)

(72) Inventor: Brian Hewko, Bay Village, OH (US)

(73) Assignee: Globus Medical, Inc., Audubon, PA (US)

(*) Notice: Subject to any disclaimer, the term of this patent is extended or adjusted under 35 U.S.C. 154(b) by 14 days.

(21) Appl. No.: 14/534,382

(22) Filed: Nov. 6, 2014

(65) Prior Publication Data

US 2015/0088259 A1 Mar. 26, 2015

Related U.S. Application Data

(63) Continuation of application No. 11/838,358, filed on Aug. 14, 2007, now Pat. No. 8,906,096.

(60) Provisional application No. 60/822,460, filed on Aug. 15, 2006.

(51) Int. Cl.
*A61F 2/44* (2006.01)
*A61F 2/30* (2006.01)

(52) U.S. Cl.
CPC .......... *A61F 2/4425* (2013.01); *A61F 2/4455* (2013.01); *A61F 2002/305* (2013.01); *A61F 2002/30087* (2013.01); *A61F 2002/3092* (2013.01); *A61F 2002/30112* (2013.01); *A61F 2002/30153* (2013.01); *A61F 2002/30364* (2013.01); *A61F 2002/30367* (2013.01); *A61F 2002/30428* (2013.01); *A61F 2002/30507* (2013.01); *A61F 2002/30563* (2013.01); *A61F 2002/30566* (2013.01); *A61F 2002/30594* (2013.01); *A61F 2002/30601* (2013.01); *A61F 2002/30604* (2013.01); *A61F 2002/30607* (2013.01); *A61F 2002/30649* (2013.01);

(Continued)

(58) Field of Classification Search
CPC .......... A61F 2002/443; A61F 2/4455; A61F 2002/305; A61F 2002/30563; A61F 2002/30112
USPC .......................................... 623/17.11–17.16
See application file for complete search history.

(56) References Cited

U.S. PATENT DOCUMENTS 5,893,889 A 4/1999 Harrington
6,572,653 B1 6/2003 Simonson (Continued)

OTHER PUBLICATIONS

International Search Report dated Feb. 27. 2008 for related PCT application No. PCT/US2007/76012.

*Primary Examiner* — Christopher Beccia

(57) ABSTRACT

Intervertebral disc prostheses and methods of use. An intervertebral disc prosthesis for installation in a spinal column may include a first intervertebral plate, a second intervertebral plate, and a removable insert core. The first intervertebral plate may engage one or both of the inferior vertebral endplate and the inferior ring apophysis of a superior vertebral body. The second intervertebral plate may engage one or both of the superior vertebral endplate and the superior ring apophysis of an inferior vertebral body. The removable insert core is located between and engages the intervertebral plates. A projection projects from one of the intervertebral plates toward the other intervertebral plate. The removable insert core at least partially surrounds the projection when installed. The removable insert core is removable from between the intervertebral plates and from around the projection while the intervertebral plates and projection remain installed.

16 Claims, 4 Drawing Sheets

(52) U.S. Cl.
CPC ............... *A61F2002/30772* (2013.01); *A61F 2002/30841* (2013.01); *A61F 2002/30904* (2013.01); *A61F 2220/0025* (2013.01); *A61F 2220/0033* (2013.01); *A61F 2230/0004* (2013.01); *A61F 2230/0019* (2013.01); *A61F 2250/0062* (2013.01); *A61F 2310/00796* (2013.01)

(56) References Cited

U.S. PATENT DOCUMENTS

| | | |
|---|---|---|
| 6,579,320 B1 | 6/2003 | Gauchet et al. |
| 6,682,562 B2 | 1/2004 | Viart et al. |
| 6,733,532 B1 | 5/2004 | Gauchet et al. |
| 6,893,465 B2 * | 5/2005 | Huang ............... A61F 2/442 623/17.12 |
| 6,899,735 B2 | 5/2005 | Coates et al. |
| 6,981,989 B1 * | 1/2006 | Fleischmann ........ A61F 2/442 623/17.11 |
| 7,011,685 B2 | 3/2006 | Arnin et al. |
| 7,044,969 B2 | 5/2006 | Errico et al. |
| 7,052,515 B2 | 5/2006 | Simonson |
| 7,083,651 B2 * | 8/2006 | Diaz ............... A61F 2/4425 623/17.13 |
| 7,563,286 B2 * | 7/2009 | Gerber ............... A61F 2/442 623/17.14 |
| 2003/0074070 A1 * | 4/2003 | Errico ............... A61F 2/442 623/17.14 |
| 2005/0143824 A1 * | 6/2005 | Richelsoph ........ A61F 2/4425 623/17.16 |
| 2005/0228500 A1 * | 10/2005 | Kim ............... A61F 2/442 623/17.13 |
| 2005/0251260 A1 * | 11/2005 | Gerber ............... A61F 2/442 623/17.13 |
| 2005/0267581 A1 | 12/2005 | Marnay et al. |
| 2006/0009850 A1 | 1/2006 | Frigg et al. |
| 2006/0041314 A1 | 2/2006 | Millard |
| 2006/0122703 A1 * | 6/2006 | Aebi ............... A61F 2/4425 623/17.15 |
| 2006/0200243 A1 | 9/2006 | Rothman |
| 2006/0217809 A1 | 9/2006 | Albert et al. |
| 2007/0233255 A1 * | 10/2007 | Song ............... A61F 2/4425 623/17.11 |

\* cited by examiner

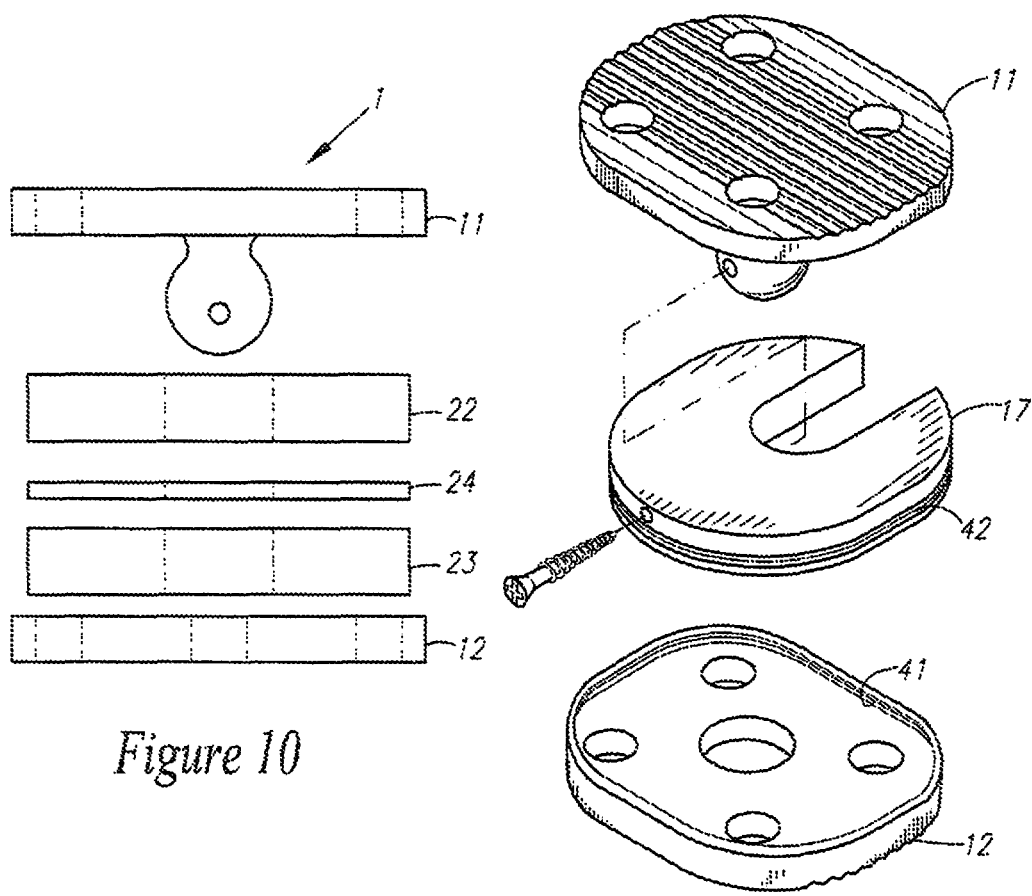
Figure 10
Figure 12
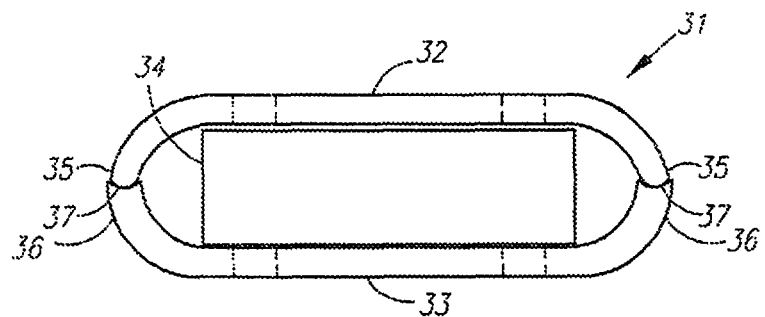
Figure 11

SPINAL IMPLANT

CROSS-REFERENCE TO RELATED APPLICATIONS

This application is a continuation of U.S. application Ser. No. 11/838,358 filed Aug. 14, 2007, which claims priority to U.S. Provisional Application Ser. No. 60/822,460 filed on Aug. 15, 2006, the contents of which are incorporated herein by reference in their entireties for all purposes.

BACKGROUND OF THE INVENTION

1. Field of the Invention

The present invention relates to spinal implants and, more particularly to intervertebral disc prostheses.

2. Description of Related Art

The spinal column comprises a series of vertebrae stacked on top of each other. There are typically seven cervical (neck), twelve thoracic (chest), and five lumbar (low back) segments. Each vertebra has a cylindrical shaped vertebral body in the anterior portion of the spine with an arch of bone to the posterior, which covers the neural structures. Each vertebral body includes superior and inferior endplates, which are respectively surrounded by superior and inferior bony rings, called ring apophyses. Between each vertebral body is an intervertebral disc, a cartilaginous cushion to help absorb impact and dampen compressive forces on the spine. To the posterior, the laminar arch covers the neural structures of the spinal cord and nerves for protection. At the junction of the arch and anterior vertebral body are articulations to allow movement of the spine.

Various types of problems can affect the structure and function of the spinal column. These can be based on degenerative conditions of the intervertebral disc or the articulating joints, traumatic disruption of the disc, bone or ligaments supporting the spine, tumor or infection. In addition congenital or acquired deformities can cause abnormal angulation or slippage of the spine. Slippage (spondylolisthesis) anterior of one vertebral body on another can cause compression of the spinal cord or nerves. Patients who suffer from one of more of these conditions often experience extreme and debilitating pain and can sustain permanent neurological damage if the conditions are not treated appropriately.

One treatment for spinal diseases and injuries is the removal and replacement of the intervertebral disc with a prosthetic device. Some intervertebral prosthetic devices provide a degree of pivotal and rotational movement, while others promote fusion of adjacent vertebrae. It would be desirable to provide an intervertebral disc prosthesis that initially provides relative movement between adjacent vertebrae, and which can be modified after installation to provide fusion of the adjacent vertebrae.

BRIEF SUMMARY OF THE INVENTION

In accordance with one aspect of the present invention, provided is an intervertebral disc prosthesis for installation in a spinal column. The prosthesis includes a first intervertebral plate for engaging one or both of the inferior vertebral endplate and the inferior ring apophysis of a superior vertebral body. A second intervertebral plate engages one or both of the superior vertebral endplate and the superior ring apophysis of an inferior vertebral body. A removable insert core is located between and engages the intervertebral plates. A projection projects from one of the intervertebral plates toward the other intervertebral plate. The removable insert core at least partially surrounds the projection when installed. The removable insert core is removable from between the intervertebral plates and from around the projection while the intervertebral plates and projection remain installed.

In accordance with another aspect of the present invention, provided is an intervertebral disc prosthesis for installation in a spinal column. The prosthesis includes a first intervertebral plate for engaging one or both of the inferior vertebral endplate and the inferior ring apophysis of a superior vertebral body. The first intervertebral plate has an aperture for permitting bone growth from the superior vertebral body through the first intervertebral plates and has a plurality of upwardly projecting teeth. A second intervertebral plate engages one or both of the superior vertebral endplate and the superior ring apophysis of an inferior vertebral body. The second intervertebral plate has another aperture for permitting bone growth from the inferior vertebral body through the second intervertebral plate, and has a plurality of downwardly projecting teeth. A removable insert core is located between and engages the intervertebral plates. The removable insert core is a resilient core having a generally C-shaped upper and lower profile. The removable insert core permits relative movement between the first intervertebral plate and the second intervertebral plate. A downward projection, having a rounded distal end, projects downward from the first intervertebral plate toward the second intervertebral plate. The second intervertebral plate forms a recessed portion for receiving the rounded distal end of the downward projection. The removable insert core at least partially surrounds the downward projection when installed in the prosthesis. The removable insert core is removable from between the intervertebral plates and from around the downward projection while the intervertebral plates and projection remain installed.

In accordance with another aspect of the present invention, provided is an intervertebral disc prosthesis for installation in a spinal column. The prosthesis includes a first intervertebral plate for engaging the endplate of a first vertebral body. A second intervertebral plate engages the endplate of a second vertebral body that is adjacent to the first vertebral body. A projection projects from one of said intervertebral plates toward the other one of said intervertebral plates. A generally C-shaped removable insert core is located between the intervertebral plates and partially surrounds the projection. The generally C-shaped removable insert core is removable from between the intervertebral plates and from around the projection while the intervertebral plates and projection remain installed.

In accordance with another aspect of the present invention, provided is an intervertebral disc prosthesis for installation in a spinal column. The prosthesis includes a first intervertebral plate for engaging one or both of the inferior vertebral endplate and the inferior ring apophysis of a superior vertebral body. A second intervertebral plate engages one or both of the superior vertebral endplate and the superior ring apophysis of an inferior vertebral body. A removable insert core is located between and engages the intervertebral plates. Upper retaining tabs project downward from peripheral portions of the first intervertebral plate. Lower retaining tabs project upward from peripheral portions of the second intervertebral plate and correspond to the upper retaining tabs. The removable insert core is radially positioned along the spinal column between said retaining tabs. The removable insert core is removable from between the intervertebral plates and retaining tabs while the intervertebral plates remain installed.

BRIEF DESCRIPTION OF THE DRAWINGS

FIG. 10 is a front elevation view of an example embodiment of an intervertebral disc prosthesis;

FIG. 11 is a front elevation view of an example embodiment of an intervertebral disc prosthesis; and FIG. 12 is a perspective view of an example embodiment of an intervertebral disc prosthesis.

DETAILED DESCRIPTION OF THE INVENTION

Figure 1:
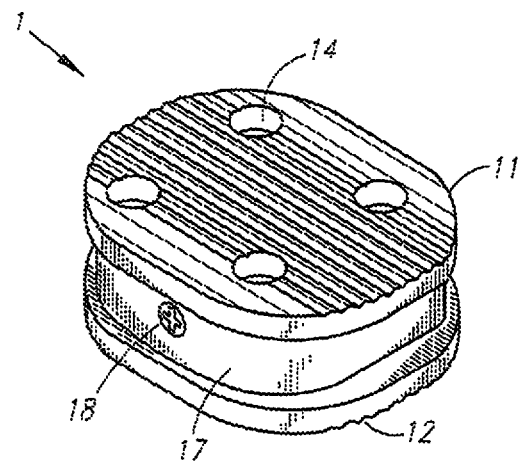
FIG. 1 is a perspective view of an example embodiment of an intervertebral disc prosthesis.
Figure 2:
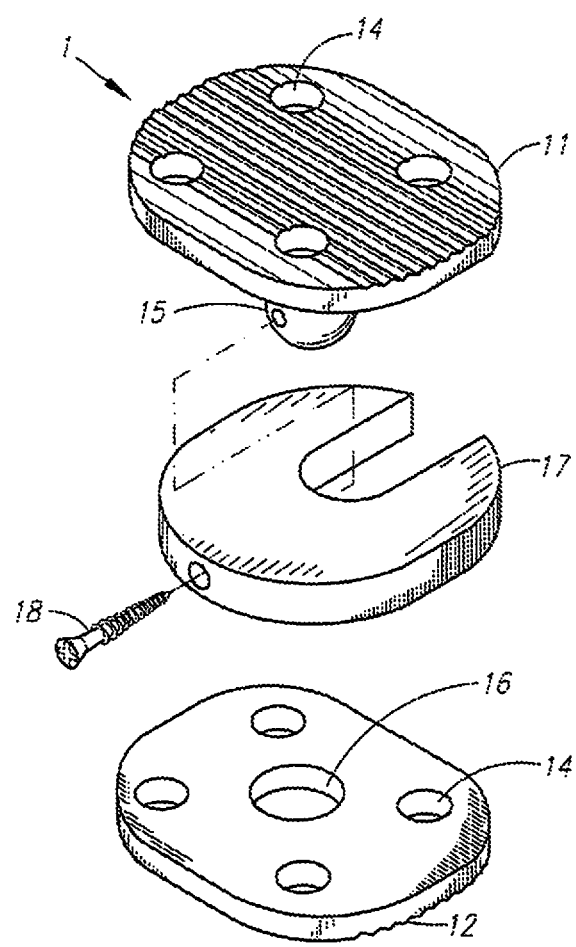
FIG. 2 is an exploded perspective view of the intervertebral disc prosthesis.
Figure 3:
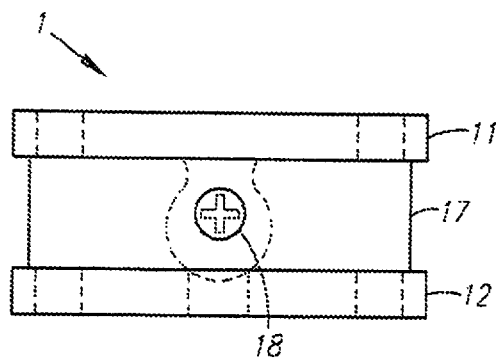
FIG. 3 is a front elevation view of the intervertebral disc prosthesis.

The present invention relates to spinal implants. The present invention will now be described with reference to the drawings, wherein like reference numerals are used to refer to like elements throughout. It is to be appreciated that the various drawings are not necessarily drawn to scale from one figure to another nor inside a given figure, and in particular that the size of the components are arbitrarily drawn for facilitating the understanding of the drawings. In the following description, for purposes of explanation, numerous specific details are set forth in order to provide a thorough understanding of the present invention. It may be evident, however, that the present invention can be practiced without these specific details. Additionally, other embodiments of the invention are possible and the invention is capable of being practiced and carried out in ways other than as described. The terminology and phraseology used in describing the invention is employed for the purpose of promoting an understanding of the invention and should not be taken as limiting.

Example embodiments of an intervertebral disc prosthesis 1 for installation in a spinal column are shown in FIGS. 1-11. The intervertebral disc prosthesis 1 is designed to be inserted anteriorly been adjacent superior (upper) and inferior (lower) vertebral bodies, to replace a removed disc.

The intervertebral disc prosthesis 1 includes a first intervertebral plate 11 and a second intervertebral plate 12. The first intervertebral plate 11 engages the superior vertebral body. More specifically, the first intervertebral plate 11 engages one or both of the inferior vertebral endplate of the vertebral body and the inferior ring apophysis of the vertebral body. The second intervertebral plate 12 engages an adjacent, inferior vertebral body. More specifically, the second intervertebral plate 12 engages one or both of the superior vertebral endplate of the adjacent vertebral body and the superior ring apophysis of the adjacent vertebral body.

The intervertebral plates 11, 12 can have a generally planar shape. Alternatively, the intervertebral plates 11, 12 can also have a curved shape, to better match the curved end face of a vertebral body.

Figure 4:
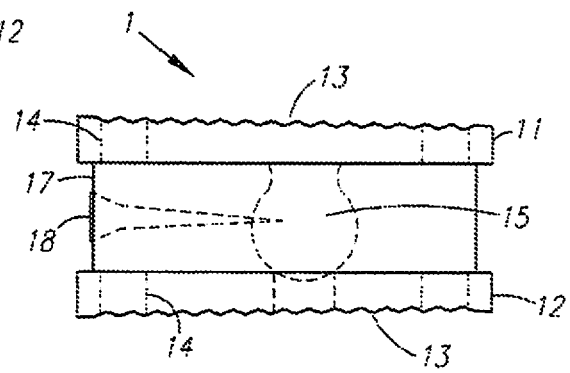
FIG. 4 is a side elevation view of the intervertebral disc prosthesis.
Figure 5:
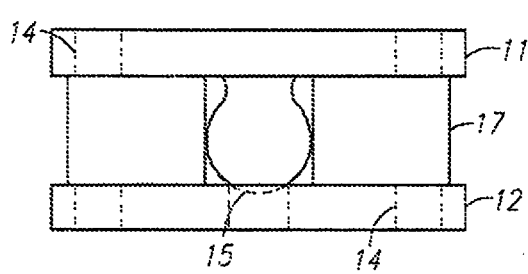
FIG. 5 is a rear elevation view of the intervertebral disc prosthesis.
Figure 6:
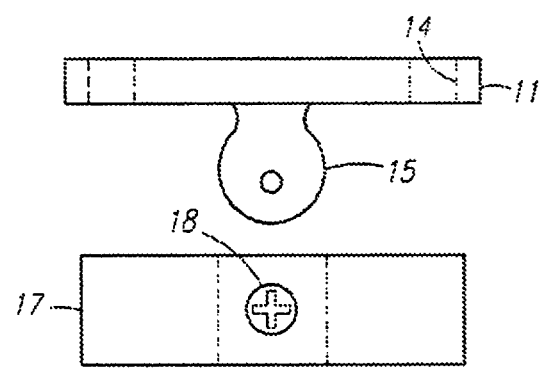
FIG. 6 is a is a front exploded view of intervertebral disc prosthesis.

As can be seen FIG. 4, the intervertebral plates 11, 12 include a plurality of teeth 13 for anchoring the plates 11, 12 to their respective vertebral bodies. In an example embodiment, the intervertebral plates 11, 12 have serrations, which provide a saw-toothed side or front profile, and which allow the plates to dig into and thereby anchor to adjacent vertebral bodies. The plurality of teeth 13 can also be in the form of a plurality of pointed spikes.

In an example embodiment, the intervertebral plates 11, 12 include a plurality of apertures 14 or recessed portions. The apertures 14 or recessed portions permit bone growth from the engaged vertebral bodies into the intervertebral plates 11, 12. The intervertebral plates 11, 12 can also be coated with a porous material, to permit bone growth into the porous material from the engaged vertebral bodies. For example, the intervertebral plates 11, 12 can include a hydroxyapatite coating.

One of the intervertebral plates, for example, the first intervertebral plate 11 includes a projection 15, which projects toward the other intervertebral plate. The projection 15 can have short, generally cylindrical main body that attaches to the intervertebral plate at a proximal end, and a rounded, knoblike distal end, as shown in the figures. It is to be appreciated that the projection 15 can take other forms, such as rod or tab, for example, and can be provided on either of the intervertebral plates 11, 12. The projection 15 helps ensure proper axial and radial positioning of the intervertebral plates 11, 12 within the spinal column. The intervertebral plate that lacks the projection 15 can include a recessed portion or aperture 16 for receiving the distal end of the projection 15. The distal end of the projection 15 rests in the aperture 16 and can pivot and rotate within the aperture 16, which allows relative movement between the intervertebral plates 11, 12. The projection 15 also serves to position and retain a removable insert core 17 between the intervertebral plates 11, 12. In an embodiment, the projection 15 includes a spring (not shown) that permits axial movement between the intervertebral plates 11, 12 along the spinal column.

The kinematics of the spine can be described by a range of rotation around an instant Axis of Rotation (IAR)/Helical Axis of Motion (HAM). The projection 15 and aperture 16 can be located along the instant axis of rotation to allow the prosthesis 1 to better replicate the motion of a spinal disc. As can be seen in, for example, FIG. 2, the projection 15 and aperture 16 can be located slightly toward the posterior of the prosthesis 1, in accordance with the instant axis of rotation. However, it is to be appreciated that the projection 15 and aperture 16 can be located in other positions, such as toward an anterior portion or lateral portion of the prosthesis 1.

Example materials of construction for the intervertebral plates include metals such as stainless steel, titanium alloys, and cobalt-chrome-molybdenum alloys, or a bio-inert polymer, for example polyetheretherketones, such as the PEEK-OPTIMA® product, which is commercially available from Invibio, Ltd.

The removable insert core 17 has a generally C-shaped upper and lower profile and fits around the projection 15. The removable insert core 17 can be removably attached to the projection 15 by elastic and friction forces provided by the removable insert core 17. For example, the removable insert core 17 can "hug" the projection and is retained between the intervertebral plates 11, 12 by hugging the projection 15. The knoblike distal end of the projection 15 can further aid in positioning and retaining the removable insert core 17. Additionally or alternatively, the removably insert core 17 can be secured to the projection 15 or one or both intervertebral plates 11, 12 via a fastener, such as a screw 18.

The removable insert core 17 is located between and operatively engages the intervertebral plates 11, 12. For example, relative movement between the intervertebral plates 11, 12 can apply force to the removable insert core 17, which resists such relative movement. The removable insert core 17 can directly engage the intervertebral plates 11, 12, by direct contact with the plates, or can indirectly engage the plates through, for example, a spacer (not shown).

The removable insert core 17 can be constructed from a resilient, generally flexible material, or a rigid, generally inflexible material. A resilient removable insert core 17 will allow relative movement between the intervertebral plates 11, 12. However, such relative movement can be constrained by the insert 17, based on the physical properties of the insert 17. An example material of construction for a resilient removable insert core 17 is an elastomeric material, such as silicon or polyethylene. The removable insert core 17 could also be constructed from a polymer, such as the PEEK-OPTIMA® product which is commercially available from Invibio, Ltd. A rigid removable insert core 17 will prevent relative movement between the intervertebral plates 11, 12, and will provide fusion between vertebrae. A rigid removable insert core 17 can include one or more passageways, to allow bone growth through the passageways. Example materials of construction for a rigid removable insert core 17 include metals, such as stainless steel, titanium alloys, and cobalt-chrome-molybdenum alloys, ceramics, and polymers, such as the PEEK-OPTIMA® product, which is commercially available from Invibio, Ltd.

The removable insert core 17 is removable from between the intervertebral plates 11, 12 and from around the projection 15. The removable insert core 17 is removable while the intervertebral plates 11, 12 remain installed in a spinal column. In the embodiments of FIGS. 1-9, the removable insert core 17 is removed by first withdrawing the screw 18, then pulling the insert 17 away from the projection 15. The projection 15 maintains proper spacing between the intervertebral plates 11, 12 while the removable insert core 17 is removed. Additional temporary bracing can be provided to prevent undesirable relative movement between the intervertebral plates 11, 12 while the removable insert core 17 is removed. A new removable insert core 17 with similar or different properties when compared to the removed insert can be installed between the intervertebral plates 11, 12. For example, a resilient removable insert core 17 can be removed from a previously installed disc prosthesis, and replaced with a rigid insert. Such a change will modify a flexible prosthesis so that it becomes a fusion-type prosthesis.

Figure 8:
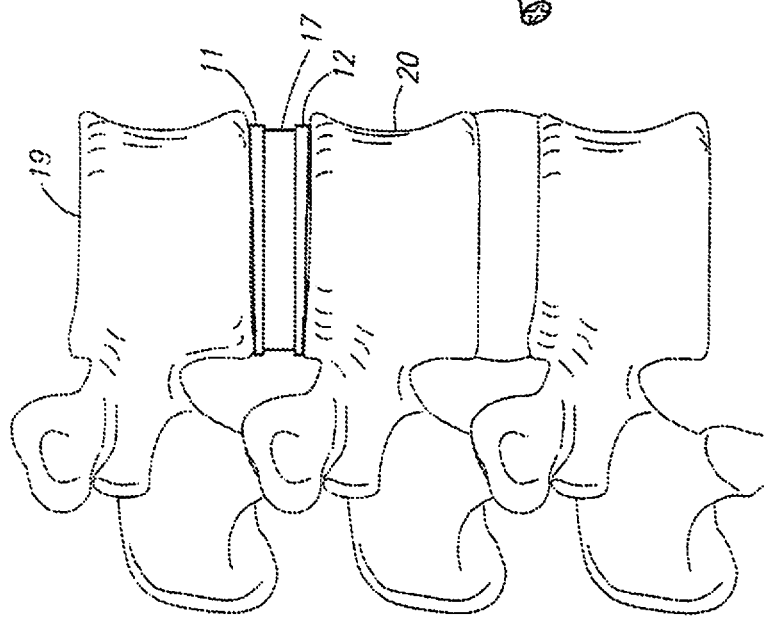
FIG. 8 shows the intervertebral disc prostheses installed in a spinal column.
Figure 7A:
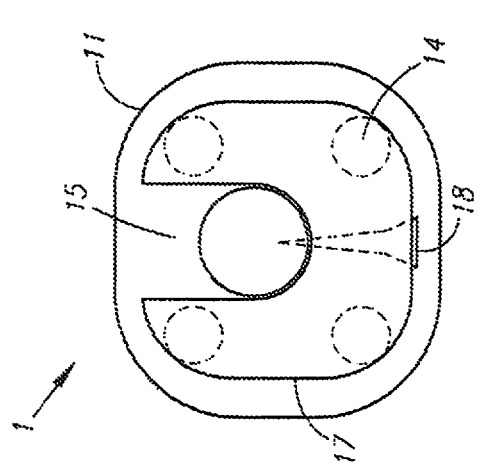
FIG. 7a is a plan view of a first intervertebral plate and assembled removable insert core.
Figure 7B:
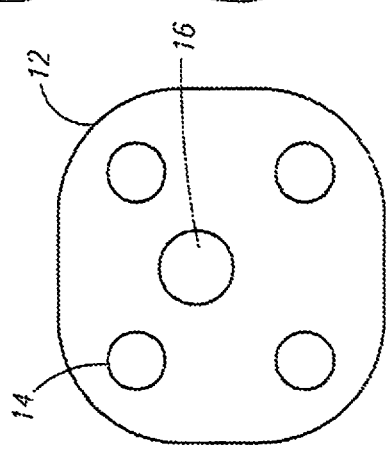
FIG. 7b is a plan view of a second intervertebral plate.

FIG. 8 shows the intervertebral disc prosthesis 1 installed between adjacent superior 19 and inferior 20 vertebral bodies. The prosthesis is installed by first removing a diseased or otherwise damaged disc. Then the intervertebral plates 11, 12 are respectively pressed into the superior 19 and inferior 20 vertebral bodies. The teeth 13 on the intervertebral plates help secure the plates 11, 12 to the vertebral bodies, by digging into the vertebral endplates and/or the ring apophyses. A removable insert core 17 having, for example, a desired rigidity or flexibility is chosen and is inserted between the intervertebral plates 11, 12 and around the projection 15. It is to be appreciated that a suitable removable insert core 17 can be selected based on additional criteria, such as durability, compatibility with the intervertebral plates 11, 12, ability to adhere to the intervertebral plates 11, 12 and or the projection 15, etc. As discussed above, the removable insert core 17 has a generally C-shaped upper and lower profile. It may be desirable to temporarily stretch open or widen the C-shaped profile, to facilitate the placement of the removable insert core 17 around the projection 15. A suitable tool can be used for this purpose. After the removable insert core is inserted between the intervertebral plates 11, 12, the fastening device is applied to secure the removable insert core to the projection 15. Alternatively, the removable insert core 17 can be secured directly to the intervertebral plates 11, 12 themselves. If desired, the installed removable insert core 17 can be removed and replaced with another core, while the intervertebral plates 11, 12 remain attached to their respective vertebral bodies.

Figure 9:
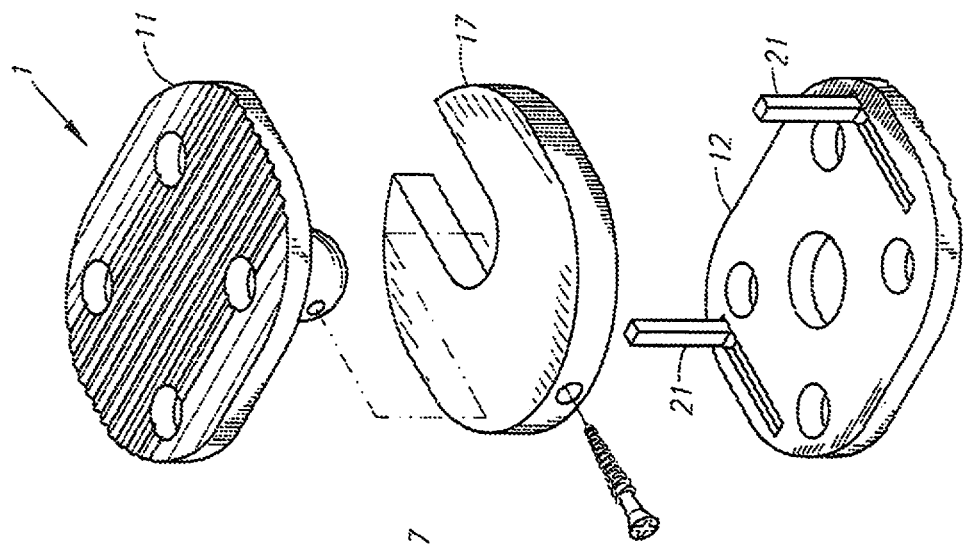
FIG. 9 is a perspective view of an example embodiment of an intervertebral disc prosthesis.

Turning to FIG. 9, in an example embodiment, the intervertebral disc prosthesis 1 includes means for selectively preventing relative movement between the intervertebral plates 11, 12. As discussed above, when a resilient removable insert core 17 is installed in the prosthesis 1, relative movement between the intervertebral plates 11, 12 can occur. One method of preventing such relative movement, for example, when fusion is desired, is by replacing the resilient insert core with a rigid insert core. Another method of preventing such relative movement is by activating a selectively deployable blocking mechanism, to block relative movement in certain directions between the intervertebral, plates 11, 12. For example, the blocking mechanism can include deployable pivot arms 21 that block relative movement between the intervertebral plates 11, 12. The pivot arms 21 are selectively deployable, and can be activated when needed. In an embodiment, the pivot arms 21 are spring-biased in the deployed, generally vertical, position, and can be held in a retained, generally horizontal, position. When a trigger, such as a lever or switch, is activated, the spring-biased pivot arms 21 are released to the deployed position. The deployed pivot arms 21 prevent relative movement between the intervertebral plates. If desired, the pivot arms 21 can be rotated back to and locked in the retained position, for later redeployment if desired. It is to be appreciated that the pivot arms 21 can be located on either intervertebral plate 11, 12 and need not be spring-biased.

In an embodiment, the resilient insert core is constructed from a material such that the properties of the resilient insert core can be changed via piezoelectric stimulation. For example, the resilient insert core can be made rigid via piezoelectric stimulation. This mitigates the need to remove and replace the insert core, should a change to a fusion-type prosthesis be desired. Electronics can be provided within the prosthesis itself, which are activated from outside the body, to provide the piezoelectric stimulation necessary to change the properties of the insert core.

Turning to FIG. 10 in an example embodiment, the intervertebral disc prosthesis 1 includes a first removable insert core 22, a second removable insert core 23, and a stabilizer plate 24 located between the first and second removable insert cores 22, 22. The stabilizer plate 24 can be a generally planar metallic plate. Together, the removable insert cores 22, 23 and the stabilizer plate 24 can form a stack having a generally C-shaped, upper and lower profile, as discussed above with respect to the removable insert core 17 of FIGS. 1-8. Any one or more of the first removable insert core 22, the second removable insert core 23, and the stabilizer plate 24 can be removed and replace, as desired. The stabilizer plate 24 adds additional rigidity to the removable insert cores 22, 22.

Turning to FIG. 11, in an example embodiment, an intervertebral disc prosthesis 31 includes a first intervertebral plate 32, a second intervertebral plate 33, and a removable insert core 34 located between the intervertebral plates 32, 33. In the embodiment of FIG. 11, the removable insert core 34 need not be generally C-shaped, although it can be generally C-shaped, or some other shape, such as a circular or elliptical cylinder. Further, the projection discussed above need not be included, although it can be included. The first intervertebral plate 32 includes upper retaining tabs 35 that project downward from peripheral portions of the first intervertebral plate 32. The second intervertebral plate 33 includes corresponding lower retaining tabs 36 that project upward from peripheral portions of the second intervertebral plate 33. The retaining tabs 35, 36 radially position and retain the removable insert core 34 along the spinal column and between the intervertebral plates 32, 33. The intervertebral plates 32, 33 can each include one large retaining tab or a plurality of smaller retaining tabs.

In an embodiment, the lower retaining tabs 36 include a channel 37 for receiving a distal portion of the upper retaining tab 35. The channel 37 helps to limit relative movement between the intervertebral plates 32, 33. Further, means for selectively preventing relative movement between the intervertebral plates 32, 33 can be provided, such as the deployable blocking mechanism discussed above.

Like the above-discussed embodiments, the embodiment of FIG. 11 can include either a resilient or rigid removable insert core 34. A rigid removable insert core 34 can include one or more passageways, to allow bone growth through the passageways. Further, the intervertebral plates 32, 33 can include apertures for permitting bone growth from the vertebral bodies into and through the apertures.

In an example embodiment, the second intervertebral plate 12 includes an inwardly protecting raised lip 41 and the removable insert core 17 includes a corresponding groove 42. When the removable insert core 17 is pressed into the second intervertebral plate 12, the inwardly projecting raised lip 41 locks into the groove 42, which locks the intervertebral plates 11, 12 and removable insert core together. The prosthesis can initially be provided with a slightly oversized resilient removable insert core, which rests on top of the raised lip 41 on the second intervertebral plate 12. When it is desired to change to a fusion-type prosthesis, the oversized resilient core can be removed and a rigid insert core having the groove 42 can be installed. The lip and groove system, along with the rigid insert core, locks the prosthesis firmly together.

The embodiments described above can preferably be used to support adjacent cervical vertebrae in the anterior region of the vertebrae. However, persons skilled in the art would recognize that the disclosed embodiments may be utilized to support adjoining thoracic and lumbar vertebrae in the anterior, lateral or posterior regions of the vertebrae. Further, the disclosed embodiments can be used to join other pieces of bone in other parts of the body.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A method of installing an intervertebral disc prosthesis in a spinal column, comprising:
    inserting an intervertebral disc prosthesis into a disc space, the intervertebral disc prosthesis including:
        a first intervertebral plate for engaging one or both of an inferior vertebral endplate and an inferior ring apophysis of a superior vertebral body,
        a second intervertebral plate for engaging one or both of a superior vertebral endplate and a superior ring apophysis of an inferior vertebral body,
        a gap located between the first and second intervertebral plates, and
        a projection that projects from one of said intervertebral plates toward the other one of said intervertebral plates, wherein the projection extends into an aperture formed in the other one of the said intervertebral plates, wherein the aperture is sized and dimensioned to receive at least a portion of the projection;
    inserting a removable insert core in the gap between the first and second intervertebral plates, the removable insert core having a first upper surface that contacts the first intervertebral plate and a second lower surface that contacts the second intervertebral plate; and
    removing the removable insert core while the intervertebral plates remain installed in the disc space, wherein the projection maintains proper spacing between the intervertebral plates while the insert core is removed.

2. The method of claim 1 further comprising, after inserting the removable insert core, securing a fastening device through the removable insert core and into the projection.

3. The method of claim 1, wherein the removable insert core is a resilient core that permits relative movement between the first intervertebral plate and the second intervertebral plate.

4. The method of claim 1 further comprising replacing the removable insert core with a second insert core having different properties than the removable insert core.

5. The method of claim 4, wherein the second insert core is rigid and is configured to promote fusion.

6. The method of claim 1 further comprising, after inserting the removable insert core, deploying a blocking mechanism to block relative movement between the intervertebral plates.

7. The method of claim 6, wherein the blocking mechanism includes at least one deployable pivot arm.

8. The method of claim 1 further comprising, before inserting the intervertebral disc prosthesis into the disc space, removing at least a portion of a diseased or damaged disc to create the disc space.

9. The method of claim 1, wherein the removable insert core has a generally C-shaped upper and lower profile.

10. The method of claim 1, wherein the first intervertebral plate includes a porous coating for engaging the superior vertebral body and permitting bone growth into the porous coating from the superior vertebral body, and wherein the second intervertebral plate includes another porous coating for engaging the inferior vertebral body and permitting bone growth into the another porous coating from the inferior vertebral body.

11. The method of claim 1, wherein the first intervertebral plate forms a plurality of apertures for permitting bone growth from the superior vertebral body through the first intervertebral plate, and wherein the second intervertebral plate forms a second plurality of apertures for permitting bone growth from the inferior vertebral body through the second intervertebral plate.

12. The method of claim 1, wherein the first intervertebral plate and the second intervertebral plate each include respective vertebral engaging surfaces having saw-toothed side profiles.

13. A method of installing an intervertebral disc prosthesis in a spinal column, comprising:
  inserting an intervertebral disc prosthesis into a disc space, the intervertebral disc prosthesis including:
    a first intervertebral plate for engaging one or both of an inferior vertebral endplate, and
    a second intervertebral plate for engaging one or both of a superior vertebral endplate,
    a gap located between the first and second intervertebral plates, and
    a projection that projects from one of said intervertebral plates toward the other one of said intervertebral plates, wherein the projection extends into an aperture formed in the other one of the said intervertebral plates, wherein the aperture is sized and dimensioned to receive at least a portion of the projection;
  inserting a removable insert core in the gap between the first and second intervertebral plates, the removable insert core having a first upper surface that contacts the first intervertebral plate and a second lower surface that contacts the second intervertebral plate; and
  removing the removable insert core while the intervertebral plates remain installed in the disc space, wherein the projection maintains proper spacing between the intervertebral plates while the insert core is removed.

14. The method of claim 13 further comprising, after inserting the intervertebral disc prosthesis into the disc space, inserting a removable insert core in the gap between the first and second intervertebral plates, the removable insert core having a first upper surface that contacts the first intervertebral plate and a second lower surface that contacts the second intervertebral plate.

15. A method of installing an intervertebral disc prosthesis in a spinal column, comprising:
  inserting an intervertebral disc prosthesis into a disc space, the intervertebral disc prosthesis including:
    a first intervertebral plate for engaging one or both of an inferior vertebral endplate and an inferior ring apophysis of a superior vertebral body,
    a second intervertebral plate for engaging one or both of a superior vertebral endplate and a superior ring apophysis of an inferior vertebral body,
    a removable insert core positioned between the first and second intervertebral plates, the removable insert core having a first upper surface that contacts the first intervertebral plate and a second lower surface that contacts the second intervertebral plate, and
    a projection that projects from one of said intervertebral plates toward the other one of said intervertebral plates, wherein the projection extends at least an entire height of the removable insert core and into an aperture formed in the other one of the said intervertebral plates, wherein the aperture is sized and dimensioned to receive at least a portion of the projection; and
  removing the removable insert core while the first and second intervertebral plates remain installed in the disc space.

16. The method of claim 15 further comprising replacing the removable insert core with a second insert core having different properties than the removable insert core.

* * * * *